United States Patent
Krasheninnik et al.

(10) Patent No.: US 11,357,185 B2
(45) Date of Patent: *Jun. 14, 2022

(54) POLYNUCLEOTIDES AND KITS ASSOCIATED WITH SOYBEAN IRON DEFICIENCY TOLERANCE AND METHODS OF DETECTION AND BREEDING

(71) Applicant: PIONEER HI-BRED INTERNATIONAL, INC., Johnston, IA (US)

(72) Inventors: Nadia Nikolayevna Krasheninnik, Fargo, ND (US); Landon Linn Ries, Armstrong, IA (US); Joshua Michael Shendelman, Ankeny, IA (US); Jordan Dustin Spear, Ankeny, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 134 days.

This patent is subject to a terminal disclaimer.

(21) Appl. No.: 16/740,585

(22) Filed: Jan. 13, 2020

(65) Prior Publication Data

US 2020/0128770 A1 Apr. 30, 2020

Related U.S. Application Data

(62) Division of application No. 15/544,339, filed as application No. PCT/US2016/012484 on Jan. 7, 2016, now Pat. No. 10,555,467.

(60) Provisional application No. 62/109,147, filed on Jan. 29, 2015.

(51) Int. Cl.
| | |
|---|---|
| *C12Q 1/6895* | (2018.01) |
| *A01H 6/54* | (2018.01) |
| *A01H 1/04* | (2006.01) |
| *A01H 1/02* | (2006.01) |

(52) U.S. Cl.
CPC .................. *A01H 1/04* (2013.01); *A01H 1/02* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 7,582,806 B2 | 9/2009 | Sebastian et al. | |
| 7,977,533 B2 | 7/2011 | Sebastian et al. | |
| 10,555,467 B2 * | 2/2020 | Krasheninnik | C12Q 1/6895 |
| 2014/0189902 A1 | 7/2014 | Chaky | |

FOREIGN PATENT DOCUMENTS

WO 2013/033221 A1 3/2013

OTHER PUBLICATIONS

Dirk V. Charlson et al., Associating SSR Markers with Soybean Resistance to Iron Deficiency Chlorosis, Journal of Plant Nutrition, 2003, pp. 2267-2276, vol. 26, Nos. 10 & 11.
Dirk V. Charlson et al., Molecular Marker Satt481 is Associated with Iron-Deficiency Chlorosis Resistance in a Soybean Breeding Population, Crop Science, 2005, pp. 2394-2399, vol. 45.
P. B. Cregan et al., An Integrated Genetic Linkage Map of the Soybean Genome, Crop Science, 1999, pp. 1464-1490, vol. 39.
Database Accession No. EI300048, GM_WBc0025N18.r GM_WBc Glycine max genomic clone GM_WBc0025N18 3-, genomic survey sequence, Feb. 16, 2007.
B. W. Diers, Possible Identification of Quantitative Trait Loci Affecting Iron Efficiency in Soybean, Journal of Plant Nutrition, 1992, pp. 2127-2136, vol. 15 No. 10.
D. L. Hyten et al., A High Density Integrated Genetic Linkage Map of Soybean and the Development of a 1536 Universal Soy Linkage Panel for Quantitative Trait Locus Mapping, Crop Science, May-Jun. 2010, pp. 960-968, vol. 50.
S. Lin et al., Mapping genetic loci for iron deficiency chlorosis in soybean, Molecular Breeding, 1997, pp. 219-229, vol. 3.
Shun Fun Lin et al., Molecular Characterization of Iron Deficiency Chlorosis in Soybean, Journal of Plant Nutrition, 2000, pp. 1929-1939, vol. 23, Nos. 11 & 12.
Jeremy Schmutz et al., Genome sequence of the palaeopolyploid soybean, Nature, Jan. 2010, pp. 178-183, vol. 463, No. 14.
Jeremy Schmutz et al., Genome sequence of the palaeopolyploid soybean, Nature, May 2010, pp. 120, vol. 465, No. 6, Correction.
International Search Report and Written Opinion, PCT/US2016/012484, dated Apr. 22, 2016.
U.S. Appl. No. 13/162,634, filed Jun. 17, 2011.
U.S. Appl. No. 14/133,807, filed Dec. 19, 2013.
U.S. Appl. No. 13/798,409, filed Mar. 13, 2013.
Mamidi et al., Genome-Wide Association Analysis Identifies Candidate Genes Associated with Iron Deficiency Chlorosis in Soybean, The Plant Genome, 4: 154-164, Aug. 2011 (and relevant portion of Supplemental Table 1).
GenBank Accession No. AC173962.20 "Glycine max clone gmw2-175d10," published Jul. 15, 2014.
Schmutz, et al., 2010, Nature, vol. 463, pp. 178-183.

* cited by examiner

*Primary Examiner* — Bratislav Stankovic

(57) ABSTRACT

Molecular markers useful for identifying, selecting, and/or providing soybean plants displaying tolerance, improved tolerance, or susceptibility to iron deficiency, methods of their use, and compositions having one or more marker loci are provided. Methods comprise detecting at least one marker locus, detecting a haplotype, and/or detecting a marker profile. Methods may further comprise crossing a selected soybean plant with a second soybean plant. Isolated polynucleotides, primers, probes, kits, systems, as well as soybean plants, seeds, and parts thereof are also provided.

15 Claims, No Drawings
Specification includes a Sequence Listing.

SEQUENCE LISTING

```
<160> NUMBER OF SEQ ID NOS: 5

<210> SEQ ID NO 1
<211> LENGTH: 400
<212> TYPE: DNA
<213> ORGANISM: Glycine max

<400> SEQUENCE: 1
aactagaaaa tgaaaataat aaattctcgt tttcagttga gaaagaaat ctcatttcgg      60 rtaaaatgaa atggtggcaa tgaatgtaat tttaagcaaa tctaaaaata caaaaagaca     120
agaagtcaat atatcataaa tttttcagtat ttttattttca tgaaaataga aaacaaaaag   180
tcaaaccaaa cgtattttca raattctaat cttttgaaaa tgaaaacagt cttcagaaaa    240
tgaaaacagg aaataaaaat agaaaatraa aatgcaaacy aaacacatyc taagggacct    300
aaaaattrct atactttgrc tatgtcttta tttaatactc ccyctgttct ctcttatgag    360
aaaaaaacaa atttttgttg tccttttataa acaaattttc                         400
```

```
<210> SEQ ID NO 2
<211> LENGTH: 16
<212> TYPE: DNA
<213> ORGANISM: Artificial sequence
<220> FEATURE:
<223> OTHER INFORMATION: S29731-001 probe1 (FAM)

<400> SEQUENCE: 2
cgtattttca gaattc                                                 16

<210> SEQ ID NO 3
<211> LENGTH: 16
<212> TYPE: DNA
<213> ORGANISM: Artificial sequence
<220> FEATURE:
<223> OTHER INFORMATION: S29731-001 Probe2 (VIC)

<400> SEQUENCE: 3
acgtattttc aaaatt                                                 16

<210> SEQ ID NO 4
<211> LENGTH: 20
<212> TYPE: DNA
<213> ORGANISM: Glycine max

<400> SEQUENCE: 4
tgaaatggtg gcaatgaatg                                             20

<210> SEQ ID NO 5
<211> LENGTH: 25
<212> TYPE: DNA
<213> ORGANISM: Glycine max

<400> SEQUENCE: 5
cctgttttca ttttctgaag actgt                                       25
```

POLYNUCLEOTIDES AND KITS ASSOCIATED WITH SOYBEAN IRON DEFICIENCY TOLERANCE AND METHODS OF DETECTION AND BREEDING

CROSS-REFERENCE TO RELATED APPLICATIONS

The present application is a divisional of U.S. patent application Ser. No. 15/544,339, filed Jul. 18, 2017, which is a 371 National Stage Entry of International Patent Application No. PCT/US16/12484, filed Jan. 7, 2016, and claims the benefit of U.S. Provisional Application No. 62/109,147, filed Jan. 29, 2015, the disclosures of which are hereby incorporated herein in their entirety by reference.

REFERENCE TO SEQUENCE LISTING SUBMITTED ELECTRONICALLY

The official copy of the sequence listing is submitted electronically via EFS-Web as an ASCII formatted sequence listing with a file named "20151217_6579PCT_Sequence-Listing.txt" created on Dec. 17, 2015 and having a size of 2 kilobytes and is filed concurrently with the specification. The sequence listing contained in this ASCII formatted document is part of the specification and is herein incorporated by reference in its entirety.

FIELD OF THE DISCLOSURE

This disclosure relates to compositions useful for identifying iron deficiency tolerant or susceptible soybean plants and methods of their use.

BACKGROUND

Soybeans (*Glycine max* L. Merr.) are a major cash crop and investment commodity in North America and elsewhere. Soybean is the world's primary source of seed oil and seed protein. Improving soybean tolerance to diverse and/or adverse growth conditions is crucial for maximizing yields. Studies have shown that even mild IDC symptoms are an indication that yield is being negatively affected (Fehr (1982) J Plant Nutr 5:611-621).

Iron-deficiency chlorosis (IDC, or FEC), reduces soybean yields. Iron is required for the synthesis of chlorophyll and, although the amount of iron is sufficient in most soils, it is often in an insoluble form that cannot be used by the plant. Iron deficiency is typically associated with soils having high pH, high salt content, cool temperatures or other environmental factors that decrease iron solubility. Chlorosis develops due to a lack of chlorophyll in the leaves of affected plants, manifesting as yellowing of the leaves.

There remains a need for soybean plants with improved tolerance to iron deficiency and methods for identifying, selecting and providing such plants, including improved markers for identifying plants possessing tolerance or susceptibility.

SUMMARY

Molecular markers useful for identifying, selecting, and/or providing soybean plants displaying tolerance, improved tolerance, or susceptibility to iron deficiency, methods of their use, and compositions having one or more marker loci are provided. Methods comprise detecting at least one marker locus, detecting a haplotype, and/or detecting a marker profile. Methods may further comprise crossing a selected soybean plant with a second soybean plant. Isolated polynucleotides, primers, probes, kits, systems, etc., are also provided.

One aspect of the disclosure features a method of detecting a first soybean plant or germplasm with improved iron deficiency tolerance, the method comprising detecting at least one favorable allele of one or more marker locus within 80 kb of a polynucleotide selected from the group consisting of: a) one or more marker loci on linkage group A1 selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525; b) a marker on linkage group A1 of S29731-001-Q001; c) one or more markers within a genomic DNA region selected from the group consisting of SEQ ID NOs: 1-5; and, d) one or more markers within a chromosome interval on linkage group A1 Gm05:9002800-Gm05:9097400.

In an aspect, said detecting comprises detection of a haplotype comprising two or more markers selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525.

In an aspect, said detecting comprises detection of a haplotype comprising marker S29731-001-Q001 and a second marker selected from the group consisting of Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525.

In an aspect, said at least one favorable allele of one or more marker loci is selected from the group consisting of S29731 allele G, Gm05:9031274 allele G, Gm05:9032977 allele A, Gm05:9009488 allele G, Gm05:8897027 allele C, Gm05:8826919 allele T, Gm05:8912496 allele G, Gm05:8915863 allele C, Gm05:9011110 allele T, Gm05:9081402 allele G, Gm05:8912289 allele G, Gm05:8994830 allele C, Gm05:8912456 allele T, Gm05:8826615 allele G, Gm05:8810680 allele C, Gm05:9098413 allele A, Gm05:8915641 allele T, Gm05:8912447 allele A, Gm05:8915642 allele A, Gm05:8915936 allele A, Gm05:8994518 allele A, Gm05:8911000 allele G, Gm05:8827043 allele C, Gm05:8808821 allele T, Gm05:8928168 allele C, Gm05:8913147 allele T, Gm05:9022152 allele A, Gm05:8822453 allele A, Gm05:8825498 allele C, Gm05:8814460 allele G, Gm05:8827199 allele C, Gm05:8827200 allele A, Gm05:8912397 allele T, Gm05:8809849 allele T, Gm05:8819720 allele T, Gm05:8826854 allele A, Gm05:8912668 allele C, Gm05:8818385 allele A, Gm05:8826076 allele G, Gm05:8913545 allele T, and Gm05:9080525 allele G.

In an aspect, the detecting comprises amplifying the marker locus or a portion of the marker locus and detecting the resulting amplified marker amplicon.

In an aspect, the amplifying comprises: admixing an amplification primer or amplification primer pair with a nucleic acid isolated from the first soybean plant or germplasm, wherein the primer or primer pair is complementary or partially complementary to at least a portion of the marker locus and is capable of initiating DNA polymerization by a DNA polymerase using the soybean nucleic acid as a template; and extending the primer or primer pair in a DNA polymerization reaction comprising a DNA polymerase and a template nucleic acid to generate at least one amplicon.

In an aspect, the admixing further comprises admixing at least one nucleic acid probe.

In an aspect, the detection comprises PCR analysis.

In an aspect, the method further comprises selecting the first soybean plant or germplasm, or selecting a progeny of the first soybean plant or germplasm.

In an aspect, the method further comprises crossing the selected first soybean plant or germplasm with a second soybean plant or germplasm.

In an aspect, the second soybean plant or germplasm comprises an exotic soybean strain or an elite soybean strain.

Another aspect of the disclosure features a kit for selecting at least one soybean plant, the kit comprising: a) primers or probes for detecting one or more marker loci associated with one or more quantitative trait loci associated with improved iron deficiency tolerance, wherein the one or more marker loci are selected from the group consisting of: i) one or more loci on linkage group A1 selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525; and ii) one or more markers within a genomic DNA region SEQ ID NOs: 1; and, b) instructions for using the primers or probes for detecting the one or more marker loci and correlating the detected marker loci with predicted improved tolerance or increased susceptibility to iron deficiency.

In an aspect, the primers or probes comprise one or more of SEQ ID NOs: 1-5.

Another aspect of the disclosure features an isolated polynucleotide capable of detecting a marker locus selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525.

In an aspect, the polynucleotide comprises a nucleotide sequence selected from the group consisting of SEQ ID NOs: 1-5.

Another aspect of the disclosure features an isolated polynucleotide capable of detecting a nucleotide polymorphism on soybean chromosome 5 wherein the polymorphism is at a genomic location selected from the group consisting of Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525.

Another aspect of the disclosure features a method of soybean plant breeding comprising: a) crossing at least two different soybean parent plants, wherein the parent soybean plants differ in iron deficiency tolerance; b) obtaining a population of progeny soybean seed from said cross; c) genotyping the progeny soybean seed with at least one genetic marker; and, d) selecting a subpopulation comprising at least one soybean seed possessing a genotype for improved iron deficiency tolerance, wherein the mean iron deficiency tolerance of the selected subpopulation is improved as compared to the mean iron deficiency tolerance of the non-selected progeny subpopulation.

Another aspect of the disclosure features a method of soybean plant breeding comprising: a) crossing two different soybean parent plants, wherein the parent soybean plants differ in iron deficiency tolerance, and the parent soybean plant with higher iron deficiency tolerance has an earlier maturity adapted for a northern growing region; b) obtaining progeny soybean seed from said cross; c) genotyping the progeny seed of said cross with a genetic marker; and, d) selecting progeny soybean seed possessing a genotype for improved iron deficiency tolerance.

In an aspect, the parent plants differ in maturity by at least 10 days.

In an aspect, the selected progeny soybean seed are adapted for a northern growing region.

SUMMARY OF SEQUENCES

SEQ ID NOs: 1-5 comprise polynucleotide sequences of regions of the soybean genome, each capable of being used as a probe or primer, either alone or in combination, for the detection of a marker locus associated with iron deficiency tolerance in soybean. In certain examples, Primer1 and Primer2 are used as allele specific primers and Probe1 and Probe2 are used as allele probes. The SEQ ID NOs provided in the "Region" column of Table 1 below are each a genomic DNA region encompassing the respective marker locus. In some examples, the primers and/or probes detect the polymorphism based on a polynucleotide complementary to the genomic region provided here. It is to be understood that the sequences provided are sufficient for one of skill in the art to detect a locus associated with iron deficiency tolerance in soybean regardless of the orientation (forward, or reverse) of the strand used for detection.

TABLE 1

| | | SEQ ID NO | | | | |
|---|---|---|---|---|---|---|
| Locus | Allele (RIS) | Region | Probe1 | Probe2 | Primer1 | Primer2 |
| S29731 | G/A | 1 | 2 | 3 | 4 | 5 |

DETAILED DESCRIPTION

Method for identifying a soybean plant or germplasm that displays tolerance, improved tolerance, or susceptibility to iron deficiency, the method comprising detecting at least one allele of one or more marker loci associated with iron deficiency tolerance are provided.

In some examples, the method involves detecting at least one marker locus associated with iron deficiency tolerance in soybean. In some examples the method comprises detecting a polymorphism flanked by and including a marker locus from Gm05:9002800-Gm05:9097400 on LG A1. In some examples the method comprises detecting at least one polymorphism within about 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 110 kb, 120 kb, 130 kb, 140 kb, 150 kb, 160 kb, 170 kb, 180 kb, 190 kb, or about 200 kb of a marker locus selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525 on LG A1. In some examples the method comprises detecting a polymorphism in a marker locus selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525. In some examples, the method comprises detecting a polymorphism using a marker of S29731-001-Q001.

In other examples, the method involves detecting a haplotype comprising two or more marker loci, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 marker loci, or more. In certain examples, the haplotype comprises two or more loci selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525. In further examples, the haplotype comprises markers from the set of markers described in Table 3.

In some examples, the one or more alleles are favorable alleles that positively correlate with tolerance or improved tolerance to iron deficiency. In other examples, the one or more alleles are disfavored alleles that positively correlate with susceptibility or increased susceptibility to iron deficiency.

In certain examples, the one or more marker locus detected comprises one or more markers on LG-A1, wherein one of the markers is S29731-001-Q001. In other examples, the one or more marker locus detected comprises one or more markers within the chromosome interval on linkage group A1 flanked by and including Gm05:9002800-Gm05:9097400. In additional examples, the one or more marker locus detected comprises one or more markers within the chromosome interval on linkage group A1 a region of about 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 110 kb, 120 kb, 130 kb, 140 kb, 150 kb, 160 kb, 170 kb, 180 kb, 190 kb, or about 200 kb comprising a marker locus selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525. In further examples, the one or more marker locus detected comprises one or more markers within one or more of the genomic DNA regions of SEQ ID NOs: 1-5. In some examples, the one or more polymorphism detected may be less than about 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 110 kb, 120 kb, 130 kb, 140 kb, 150 kb, 160 kb, 170 kb, 180 kb, 190 kb, or about 200 kb from one or more of SEQ ID NO: 1-5.

In some examples, the at least one favorable allele of one or more marker loci is selected from the group consisting of S29731 allele G, Gm05:9031274 allele G, Gm05:9032977 allele A, Gm05:9009488 allele G, Gm05:8897027 allele C, Gm05:8826919 allele T, Gm05:8912496 allele G, Gm05:8915863 allele C, Gm05:9011110 allele T, Gm05:9081402 allele G, Gm05:8912289 allele G, Gm05:8994830 allele C, Gm05:8912456 allele T, Gm05:8826615 allele G, Gm05:8810680 allele C, Gm05:9098413 allele A, Gm05:8915641 allele T, Gm05:8912447 allele A, Gm05:8915642 allele A, Gm05:8915936 allele A, Gm05:8994518 allele A, Gm05:8911000 allele G, Gm05:8827043 allele C, Gm05:8808821 allele T, Gm05:8928168 allele C, Gm05:8913147 allele T, Gm05:9022152 allele A, Gm05:8822453 allele A, Gm05:8825498 allele C, Gm05:8814460 allele G, Gm05:8827199 allele C, Gm05:8827200 allele A, Gm05:8912397 allele T, Gm05:8809849 allele T, Gm05:8819720 allele T, Gm05:8826854 allele A, Gm05:8912668 allele C, Gm05:8818385 allele A, Gm05:8826076 allele G, Gm05:8913545 allele T, and Gm05:9080525 allele G. In some examples, the SNP haplotype comprises one or more of the marker alleles selected from the group consisting of S29731 allele G, Gm05:9031274 allele G, Gm05:9032977 allele A, Gm05:9009488 allele G, Gm05:8897027 allele C, Gm05:8826919 allele T, Gm05:8912496 allele G, Gm05:8915863 allele C, Gm05:9011110 allele T, Gm05:9081402 allele G, Gm05:8912289 allele G, Gm05:8994830 allele C, Gm05:8912456 allele T, Gm05:8826615 allele G, Gm05:8810680 allele C, Gm05:9098413 allele A, Gm05:8915641 allele T, Gm05:8912447 allele A, Gm05:8915642 allele A, Gm05:8915936 allele A, Gm05:8994518 allele A, Gm05:8911000 allele G, Gm05:8827043 allele C, Gm05:8808821 allele T, Gm05:8928168 allele C, Gm05:8913147 allele T, Gm05:9022152 allele A, Gm05:8822453 allele A, Gm05:8825498 allele C, Gm05:8814460 allele G, Gm05:8827199 allele C, Gm05:8827200 allele A, Gm05:8912397 allele T, Gm05:8809849 allele T, Gm05:8819720 allele T, Gm05:8826854 allele A, Gm05:8912668 allele C, Gm05:8818385 allele A, Gm05:8826076 allele G, Gm05:8913545 allele T, and Gm05:9080525 allele G. In some examples, the SNP haplotype comprises two or more of the marker alleles selected from the group consisting of S29731 allele G, Gm05:9031274 allele G, Gm05:9032977 allele A, Gm05:9009488 allele G, Gm05:8897027 allele C, Gm05:8826919 allele T, Gm05:8912496 allele G, Gm05:8915863 allele C, Gm05:9011110 allele T, Gm05:9081402 allele G, Gm05:8912289 allele G, Gm05:8994830 allele C, Gm05:8912456 allele T, Gm05:8826615 allele G, Gm05:8810680 allele C, Gm05:9098413 allele A, Gm05:8915641 allele T, Gm05:8912447 allele A, Gm05:8915642 allele A, Gm05:8915936 allele A, Gm05:8994518 allele A, Gm05:8911000 allele G, Gm05:8827043 allele C, Gm05:8808821 allele T, Gm05:8928168 allele C, Gm05:8913147 allele T, Gm05:9022152 allele A, Gm05:8822453 allele A, Gm05:8825498 allele C, Gm05:8814460 allele G, Gm05:8827199 allele C, Gm05:8827200 allele A, Gm05:8912397 allele T, Gm05:8809849 allele T, Gm05:8819720 allele T, Gm05:8826854 allele A, Gm05:8912668 allele C, Gm05:8818385 allele A, Gm05:8826076 allele G, Gm05:8913545 allele T, and Gm05:9080525 allele G. In other examples, the haplotype comprises two or more favorable alleles from the set of alleles described in Table 3. In some examples, the haplotype may comprise a combination of favorable and unfavorable alleles.

Detecting may comprise amplifying the marker locus or a portion of the marker locus and detecting the resulting amplified marker amplicon. In particular examples, the amplifying comprises admixing an amplification primer or amplification primer pair and, optionally at least one nucleic acid probe, with a nucleic acid isolated from the first soybean plant or germplasm, wherein the primer or primer pair and optional probe is complementary or partially complementary to at least a portion of the marker locus and is capable of initiating DNA polymerization by a DNA polymerase using the soybean nucleic acid as a template; and, extending the primer or primer pair in a DNA polymerization reaction comprising a DNA polymerase and a template nucleic acid to generate at least one amplicon. In particular examples, the detection comprises real time PCR analysis.

In still further aspects, the information disclosed herein regarding marker alleles and SNP haplotypes can be used to aid in the selection of breeding plants, lines, and populations containing tolerance to iron deficiency, and/or for use in introgression of this trait into elite soybean germplasm, exotic soybean germplasm, or any other soybean germplasm. Also provided is a method for introgressing a soybean QTL, marker, or haplotype associated with iron deficiency tolerance into non-tolerant or less tolerant soybean germplasm. According to the method, markers and/or haplotypes are used to select soybean plants containing the improved tolerance trait. Plants so selected can be used in a soybean breeding program. Through the process of introgression, the QTL, marker, or haplotype associated with improved iron deficiency tolerance is introduced from plants identified using marker-assisted selection (MAS) to other plants. According to the method, agronomically desirable plants and seeds can be produced containing the QTL, marker, or haplotype associated with iron deficiency tolerance from germplasm containing the QTL, marker, or haplotype. Sources of improved tolerance are disclosed below.

Also provided herein is a method for producing a soybean plant adapted for conferring improved iron deficiency tolerance. First, donor soybean plants for a parental line containing the tolerance QTL, marker, and/or haplotype are selected. According to the method, selection can be accomplished via MAS as explained herein. Selected plant material may represent, among others, an inbred line, a hybrid line, a heterogeneous population of soybean plants, or an individual plant. According to techniques well known in the art of plant breeding, this donor parental line is crossed with a second parental line. In some examples, the second parental line is a high yielding line. This cross produces a segregating plant population composed of genetically heterogeneous plants. Plants of the segregating plant population are screened for the tolerance QTL, marker, or haplotype. Further breeding may include, among other techniques, additional crosses with other lines, hybrids, backcrossing, or self-crossing. The result is a line of soybean plants that has improved tolerance to iron deficiency and optionally also has other desirable traits from one or more other soybean lines.

Also provided is a method of soybean plant breeding comprising crossing at least two different soybean parent plants, wherein the parent soybean plants differ in iron deficiency tolerance phenotypic, obtaining a population of progeny soybean seed from said cross, genotyping the progeny soybean seed with at least one genetic marker, and, selecting a subpopulation comprising at least one soybean seed possessing a genotype for improved iron deficiency tolerance, wherein the mean iron deficiency tolerance phenotype of the selected subpopulation is improved as compared to the mean iron deficiency tolerance phenotype of the non-selected progeny. In some examples the mean iron deficiency tolerance phenotype is determined on a scoring scale, for example a scale of 1-9, wherein plants with a score of 1 are completely susceptible and plants with a score of 9 are completely tolerant. In some examples the mean iron deficiency tolerance phenotype of the selected subpopulation of progeny is at least 0.25, 0.5, 0.75, or 1 points greater than the mean iron deficiency tolerance phenotype of the non-selected progeny. In other examples the mean iron deficiency tolerance phenotype of the selected subpopulation of progeny is at least 2, 3, 4, 5, 6, 7, or 8 points greater than the mean iron deficiency tolerance phenotype of the non-selected progeny. In some examples, the two different soybean parent plants also differ by maturity. The maturity groups of the parent plants may differ by one or more maturity subgroups, by one or more maturity groups, or by 1 or more days to maturity. In some examples the parents differ in maturity by at least 10 days, between 10 days-20 days, between 10 days-30 days, by at least 0.1, 0.2, 0.3, 0.4, 0.5, 0.6, 0.7, 0.8, or 0.9 maturity subgroups, by at least 1, 2, 3, 4, 5, 6, 7, 8, 9, 10, 11, or 12 maturity groups. In some examples one parent is adapted for a northern growing region, and the second parent is not adapted for a northern growing region. In some examples the parent adapted for a northern growing region comprises better iron deficiency tolerance than the parent not adapted for a northern growing region. In some examples, the method further comprises obtaining progeny better adapted for a northern growing region.

Soybean plants, seeds, tissue cultures, variants and mutants having improved iron deficiency tolerance produced by the foregoing methods are also provided. Soybean plants, seeds, tissue cultures, variants and mutants comprising one or more of the marker loci, one or more of the favorable alleles, and/or one or more of the haplotypes and having improved iron deficiency tolerance are provided. Also provided are isolated nucleic acids, kits, and systems useful for the identification and/or selection methods disclosed herein.

It is to be understood that this disclosure is not limited to particular aspects, which can, of course, vary. It is also to be understood that the terminology used herein is for the purpose of describing particular aspects only, and is not intended to be limiting. Further, all publications referred to herein are each incorporated by reference for the purpose cited to the same extent as if each was specifically and individually indicated to be incorporated by reference herein.

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of." Similarly, the term "consisting essentially of" is intended to include examples encompassed by the term "consisting of."

Certain definitions used in the specification and claims are provided below. In order to provide a clear and consistent understanding of the specification and claims, including the scope to be given such terms, the following definitions are provided:

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. An "amplicon" is an amplified nucleic acid, e.g., a nucleic acid that is produced by amplifying a template nucleic acid by any available amplification method.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment defined by specific flanking marker loci.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic association or linkage relationships among loci on one or more chromosomes (or linkage groups) within a given species, generally depicted in a diagrammatic or tabular form.

"Genotype" is a description of the allelic state at one or more loci in a genome.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Introgression" means the entry or introduction of a gene, QTL, marker, haplotype, marker profile, trait, or trait locus from the genome of one plant into the genome of another plant.

The terms "label" and "detectable label" refer to a molecule capable of detection. A detectable label can also include a combination of a reporter and a quencher, such as are employed in FRET probes or TAQMAN® probes. The term "reporter" refers to a substance or a portion thereof that is capable of exhibiting a detectable signal, which signal can be suppressed by a quencher. The detectable signal of the reporter is, e.g., fluorescence in the detectable range. The term "quencher" refers to a substance or portion thereof that is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between two genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

"Linkage" refers to the tendency for alleles tend to segregate together more often than expected by chance if their transmission was independent. Typically, linkage refers to alleles on the same chromosome. Genetic recombination occurs with an assumed random frequency over the entire genome. Genetic maps are constructed by measuring the frequency of recombination between pairs of traits or markers, the lower the frequency of recombination, the greater the degree of linkage.

"Linkage disequilibrium" is a non-random association of alleles at two or more loci and can occur between unlinked markers. It is based on allele frequencies within a population and is influenced by but not dependent on linkage. Linkage disequilibrium is typically detected when alleles segregate from parents to offspring with a greater frequency than expected from their individual frequencies.

"Linkage group" refers to traits or markers that co-segregate. A linkage group generally corresponds to a chromosomal region containing genetic material that encodes the traits or markers.

"Locus" is a defined segment of DNA.

A "map location," a "map position," or a "relative map position" is an assigned location on a genetic map relative to linked genetic markers where a specified marker can be found within a given species. Map positions are generally provided in centimorgans (cM), unless otherwise indicated, genetic positions provided are based on the *Glycine max* consensus map v 4.0 as provided by Hyten et al. (2010) Crop Sci 50:960-968. A "physical position" or "physical location" is the position, typically in nucleotide bases, of a particular nucleotide, such as a SNP nucleotide, on the chromosome. Unless otherwise indicated, the physical position within the soybean genome provided is based on the Glyma 1.0 genome sequence described in Schmutz et al. (2010) Nature 463:178-183, available from the Phytozome website (phytozome-dot-net/soybean).

"Mapping" is the process of defining the association and relationships of loci through the use of genetic markers, populations segregating for the markers, and standard genetic principles of recombination frequency.

"Marker" or "molecular marker" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest.

"Marker assisted selection" refers to the process of selecting a desired trait or traits in a plant or plants by detecting one or more nucleic acids from the plant, where the nucleic acid is associated with or linked to the desired trait, and then selecting the plant or germplasm possessing those one or more nucleic acids.

"Maturity Group" is an agreed-on industry division of groups of varieties, based on the zones in which they are adapted primarily according to day length and/or latitude. Soybean varieties are grouped into 13 maturity groups, depending on the climate and latitude for which they are adapted. Soybean maturities are divided into relative maturity groups (denoted as 000, 00, 0, I, II, III, IV, V, VI, VII, VIII, IX, X, or 000, 00, 0, 1, 2, 3, 4, 5, 6, 7, 8, 9, 10). These maturity groups are given numbers, with numbers 000, 00, 0 and 1 typically being adapted to Canada and the northern United States, groups VII, VIII and IX being grown in the southern regions, and Group X is tropical. Within a maturity group are sub-groups. A sub-group is a tenth of a relative maturity group (for example 1.3 would indicate a group 1 and subgroup 3). Within narrow comparisons, the difference of a tenth of a relative maturity group equates very roughly to a day difference in maturity at harvest.

"Haplotype" refers to a combination of particular alleles present within a particular plant's genome at two or more linked marker loci, for instance at two or more loci on a particular linkage group. For instance, in one example, two specific marker loci on LG A1 are used to define a haplotype for a particular plant. In still further examples, 3, 4, 5, 6, 7, 8, 9, 10, 11, 12, 13, 14, 15, 16, 17, 18, 19, 20, or more linked marker loci are used to define a haplotype for a particular plant.

As used herein, a "marker profile" means a combination of particular alleles present within a particular plant's genome at two or more marker loci which are not linked, for instance two or more loci on two or more different linkage groups or two or more chromosomes. For instance, in one example, one marker locus on LG A1 and a marker locus on another linkage group are used to define a marker profile for a particular plant. In certain other examples a plant's marker profile comprises one or more haplotypes. In some examples, the marker profile further includes at least one marker locus on LG A1 associated with iron deficiency tolerance. In some examples, the marker profile encompasses two or more loci for the same trait, such as iron deficiency tolerance. In other examples, the marker profile encompasses two or more loci associated with two or more traits of interest, such as iron deficiency tolerance and a second trait of interest.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells, and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid sequence," "nucleic acid fragment," and "oligonucleotide" are used interchangeably herein to indicate a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Tolerance and "improved tolerance" are used interchangeably herein and refer to any type of increase in resistance or tolerance to, or any type of decrease in susceptibility. A "tolerant plant" or "tolerant plant variety" need not possess absolute or complete tolerance. Instead, a "tolerant plant," "tolerant plant variety," or a plant or plant variety with "improved tolerance" will have a level of resistance or tolerance which is higher than that of a comparable susceptible plant or variety.

"Self crossing" or "self pollination" or "selfing" is a process through which a breeder crosses a plant with itself; for example, a second-generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

The term "yield" refers to the productivity per unit area of a particular plant product of commercial value. For example, yield of soybean is commonly measured in bushels of seed per acre or metric tons of seed per hectare per season. Yield is affected by both genetic and environmental factors.

An "isolated" or "purified" polynucleotide or polypeptide, or biologically active portion thereof, is substantially or essentially free from components that normally accompany or interact with the polynucleotide or polypeptide as found in its naturally occurring environment. Typically, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein, culture media, or other chemical components.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Sambrook").

Iron deficiency severely limits growth of soybeans in several regions of North America, particularly in poorly drained calcareous (heavy lime) soils in parts of Minnesota, the Dakotas, Nebraska and Iowa. Iron deficiency chlorosis is a complex plant disorder often associated with high pH soils and soils containing soluble salts where chemical conditions reduce the availability of iron. Environmental and soil conditions including compaction, excessive soil moisture and low soil temperatures can contribute to iron chlorosis severity, which can be differentially impact different areas of fields.

Iron is found in soil mainly as insoluble oxyhydroxide polymers (FeOOH) that are extremely insoluble ($10^{-17}$ M) at neutral pH. Since the optimal concentration of soluble Fe for plant growth is approximately $10^{-6}$ M, plants have at least two different strategies to access the iron they need from soil (Fox & Guerinot (1998) Ann Rev Plant Physiol Plant Mol Biol 49:669-96). Strategy I is used by all plants except grasses (Marschner et al. (1986) J Plant Nutr 9:3-7). This strategy involves a multi-step process, beginning with the plants releasing H+ ions into the soil from the roots via proton pump activity from an H+ ATPase, which lowers soil pH. The lowered pH leads to the dissociation of Fe(OH), complexes into ferrous ions. Fe(III) is reduced to the more soluble Fe(II) by a membrane-bound ferric chelate reductase located in root epidermal cells. Following reduction, a separate transport protein moves the reduced iron across the root plasma membrane. A gene IRT1 (iron regulated transporter) which codes for the transport protein has also been found in *Arabidopsis* (Eide et al. (1996) PNAS 93:5624-5628). This same transport protein has been shown to transport manganese, zinc, and cobalt as well (Korshunova et al. (1999) Plant Mol. Biol 40:37-44).

High carbonate levels in the soil are the main source of iron deficiency chlorosis in soybean. Other stresses, such as cold temperature, SCN infection, water saturated soils, or herbicide application may increase chlorosis. Bicarbonates can also impede the movement of iron to young leaves once it is absorbed by the roots (Barker & Pilbeam (ed.) 2007. Handbook of Plant Nutrition Vol. 117 ed. 1:335-337. Taylor & Francis Publ., New York, Philadelphia, Oxford, Melbourne, Stockholm, Beijing, New Delhi, Johannesburg, Singapore and Tokyo). Iron deficiency symptoms range from slight yellowing of leaves to stunting, severe chlorosis, and sometimes death of plants in affected fields.

While iron availability can be modulated environmentally to some extent (e.g., by modifying soil pH or adding soluble iron, applying foliar iron treatments, or applying iron to seed), these approaches can cause unwanted side effects in the soybean or the environment and also add to soybean production costs. Some treatments, such as iron treatment of seed, display inconsistent results in different cultivars or field environments. Despite these difficulties, most producers currently rely on the use of seed, foliar, or soil treatments to reduce iron deficiency chlorosis (see, e.g., Weirsma (2002) Cropping Issues in Northwest Minnesota 1(7):1-2; Goos & Germain (2001) Communications in Soil Science and Plant Analysis 32:2317-2323).

For some time, soybean producers have sought to develop iron deficiency tolerant plants as a cost-effective alternative or supplement to standard foliar, soil and/or seed treatments (e.g., Hintz et al. (1987) Crop Sci 28:369-370). Other studies also suggest that cultivar selection is more reliable and universally applicable than foliar sprays or iron seed treatment methods, though environmental and cultivar selection methods can also be used effectively in combination. See also, Goos & Johnson (2000) Agron J 92:1135-1139; and Goos & Johnson (2001) J Plant Nutr 24:1255-1268.

The advent of molecular genetic markers has facilitated mapping and selection of agriculturally important traits in soybean. Markers tightly linked to tolerance genes are an asset in the rapid identification of tolerant soybean lines on the basis of genotype by the use of marker assisted selection (MAS). Introgressing tolerance genes into a desired cultivar would also be facilitated by using suitable DNA markers.

Soybean cultivar improvement for iron deficiency tolerance can be performed using classical breeding methods, or, by using marker assisted selection (MAS). Genetic markers for iron deficiency tolerance/susceptibility have been identified (e.g., Lin et al. (2000) J Plant Nutr 23:1929-1939; Diers et al. (1992) J Plant Nut 15:2127-2136; Lin et al. (1997) Mol Breed 3:219-229; Charlson et al. (2003) J Plant Nutr 26:2267-2276; Charlson et al. (2005) Crop Sci 45:2394-2399). Studies suggest that marker assisted selection is particularly beneficial when selecting plants for iron deficiency tolerance (e.g., Charlson et al. (2003) J Plant Nutr 26:2267-2276).

Provided are markers, haplotypes, and/or marker profiles associated with tolerance of soybean plants to iron deficiency, as well as related primers and/or probes and methods for the use of any of the foregoing for identifying and/or selecting soybean plants with improved tolerance to iron deficiency. A method for determining the presence or absence of at least one allele of a particular marker or haplotype associated with tolerance to iron deficiency comprises analyzing genomic DNA from a soybean plant or germplasm to determine if at least one, or a plurality, of such markers is present or absent and if present, determining the allelic form of the marker(s). If a plurality of markers on a single linkage group are investigated, this information regarding the markers present in the particular plant or germplasm can be used to determine a haplotype for that plant/germplasm.

In certain examples, plants or germplasm are identified that have at least one favorable allele, marker, and/or haplotype that positively correlate with tolerance or improved tolerance. However, in other examples, it is useful to identify alleles, markers, and/or haplotypes that negatively correlate with tolerance, for example to eliminate such plants or germplasm from subsequent rounds of breeding. Plants or germplasm having tolerance or improved tolerance to iron deficiency chlorosis are provided.

Any marker associated with an iron deficiency tolerance QTL is useful. Further, any suitable type of marker can be used, including Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers known in the art or phenotypic traits may also be used as markers in the methods.

Markers that map closer to an iron deficiency tolerance QTL are generally used over markers that map farther from such a QTL. Marker loci are especially useful when they are closely linked to an iron deficiency tolerance QTL. Thus, in one example, marker loci display an inter-locus cross-over frequency of about 10% or less, about 9% or less, about 8% or less, about 7% or less, about 6% or less, about 5% or less, about 4% or less, about 3% or less, about 2% or less, about 1% or less, about 0.75% or less, about 0.5% or less, or about 0.25% or less with an iron deficiency tolerance QTL to which they are linked. Thus, the loci are separated from the QTL to which they are linked by about 10 cM, 9 cM, 8 cM, 7 cM, 6 cM, 5 cM, 4 cM, 3 cM, 2 cM, 1 cM, 0.75 cM, 0.5 cM, or 0.25 cM or less.

In certain examples, multiple marker loci that collectively make up a haplotype and/or a marker profile are investigated, for instance 2, 3, 4, 5, 6, 7, 8, 9, 10, 11, 12, 13, 14, 15, 16, 17, 18, 19, 20, 21, 22, 23, 24, 25, 26, 27, 28, 29, 30, or more marker loci.

In addition to the markers discussed herein, information regarding useful soybean markers can be found, for example, on the USDA's Soybase website, available at soybase.org. A number of soybean markers have been mapped and linkage groups created, as described in Cregan et al. (1999) Crop Sci 39:1464-90, Choi et al. (2007) Genetics 176:685-96, and Hyten, et al. (2010) Crop Sci 50:960-968, each of which is herein incorporated by reference in its entirety, including any supplemental materials associated with the publication. Many soybean markers are publicly available at the USDA affiliated soybase website (at soybase-dot-org). One of skill in the art will recognize that the identification of favorable marker alleles may be germplasm-specific. One of skill will also recognize that methods for identifying the favorable alleles are routine and well known in the art, and furthermore, that the identification and use of such favorable alleles is well within the scope of the disclosure.

The use of marker assisted selection (MAS) to select a soybean plant or germplasm based upon detection of a particular marker or haplotype of interest is provided. For instance, in certain examples, a soybean plant or germplasm possessing a certain predetermined favorable marker allele or haplotype will be selected via MAS. Using MAS, soybean plants or germplasm can be selected for markers or marker alleles that positively correlate with tolerance, without actually raising soybean and measuring for tolerance (or, contrawise, soybean plants can be selected against if they possess markers that negatively correlate with tolerance). MAS is a powerful tool to select for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some examples, molecular markers are detected using a suitable amplification-based detection method. Typical amplification methods include various polymerase based replication methods, including the polymerase chain reaction (PCR), ligase mediated methods, such as the ligase chain reaction (LCR), and RNA polymerase based amplification (e.g., by transcription) methods. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage & Caruthers (1981) Tetrahedron Letts 22:1859-1862, e.g., using a commercially available automated synthesizer, e.g., as described in Needham-VanDevanter et al. (1984) Nucl Acids Res 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the disclosure be limited to any particular primer, primer pair, or probe. For example, primers can be designed using any suitable software program, such as LASERGENE® or Primer3.

The primers are not limited to generating an amplicon of any particular size. For example, the primers used to amplify the marker loci and alleles herein are not limited to amplifying the entire region of the relevant locus. In some examples, marker amplification produces an amplicon at least 20 nucleotides in length, or alternatively, at least 50 nucleotides in length, or alternatively, at least 100 nucleotides in length, or alternatively, at least 200 nucleotides in length, or alternatively, at least 300 nucleotides in length, or alternatively, at least 400 nucleotides in length, or alternatively, at least 500 nucleotides in length, or alternatively, at least 1000 nucleotides in length, or alternatively, at least 2000 nucleotides in length or more.

PCR, RT-PCR, and LCR are common amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous references, such as Mullis et al. (1987) U.S. Pat. No. 4,683,202; Arnheim & Levinson (1990) C&EN 36-47; Kwoh et al. (1989) Proc Natl Acad Sci USA 86:1173; Guatelli et al. (1990) Proc Natl Acad Sci USA 87:1874; Lomell et al. (1989) J Clin Chem 35:1826; Landegren et al. (1988) Science 241:1077-1080; Van Brunt (1990) Biotechnology 8:291-294; Wu & Wallace (1989) Gene 4:560; Barringer et al. (1990) Gene 89:117; and Sooknanan & Malek (1995) Biotechnology 13:563-564.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype alleles, such as SNP alleles, are provided. For example, exemplary primers and probes are provided in Table 2. However, one of skill will immediately recognize that other primer and probe sequences could also be used. For instance, primers to either side of the given primers can be used in place of the given primers, so long as the primers can amplify a region that includes the allele to be detected, as can primers and probes directed to other marker loci. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the compositions and methods are not limited to the primers and probes specifically recited herein.

In certain examples, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Labeling strategies for labeling nucleic acids and their corresponding detection strategies can be found, e.g., in Haugland (1996) *Handbook of Fluorescent Probes and Research Chemicals Sixth Edition* by Molecular Probes, Inc. (Eugene, Oreg.); or Haugland (2001) *Handbook of Fluorescent Probes and Research Chemicals Eighth Edition* by Molecular Probes, Inc. (Eugene, Oreg.).

Detectable labels may also include reporter-quencher pairs, such as are employed in Molecular Beacon and TAQMAN® probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules,* 2nd ed., Academic Press, New York, 1971, the content of which is incorporated herein by reference. Examples of modifying reporters and quenchers for covalent attachment via common reactive groups that can be added to an oligonucleotide in the present disclosure may be found, for example, in Haugland (2001) *Handbook of Fluorescent Probes and Research Chemicals Eighth Edition* by Molecular Probes, Inc. (Eugene, Oreg.), the content of which is incorporated herein by reference.

In certain examples, reporter-quencher pairs are selected from xanthene dyes including fluorescein and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters is the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other examples, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In one aspect, real time PCR or LCR is performed on the amplification mixtures described herein, e.g., using molecular beacons or TAQMAN® probes. A molecular beacon (MB) is an oligonucleotide that, under appropriate hybridization conditions, self-hybridizes to form a stem and loop structure. The MB has a label and a quencher at the termini of the oligonucleotide; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone et al. (1995) Nucl Acids Res 26:2150-2155; Tyagi & Kramer (1996) Nat Biotechnol 14:303-308; Blok & Kramer (1997) Mol Cell Probes 11:187-194; Hsuih et al. (1997) J Clin Microbiol 34:501-507; Kostrikis et al. (1998) Science 279:1228-1229; Sokol et al. (1998) Proc Natl Acad Sci USA 95:11538-11543; Tyagi et al. (1998) Nat Biotechnol 16:49-53; Bonnet et al. (1999) Proc Natl Acad Sci USA 96:6171-6176; Fang et al. (1999) J Am Chem Soc 121:2921-2922; Marras et al. (1999) Genet Anal Biomol Eng 14:151-156; and, Vet et al. (1999) Proc Natl Acad Sci USA 96:6394-6399. Additional details regarding MB construction and use are also found in the patent literature, e.g., U.S. Pat. Nos. 5,925,517; 6,150,097; and 6,037,130.

Another real-time detection method is the 5'-exonuclease detection method, also called the TAQMAN® assay, as set forth in U.S. Pat. Nos. 5,804,375; 5,538,848; 5,487,972; and 5,210,015, each of which is hereby incorporated by reference in its entirety. In the TAQMAN® assay, a modified probe, typically 10-30 nucleotides in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are typically attached to the probe within a few nucleotides of one another, usually within 30 nucleotides of one another, or within 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

One example of a suitable real-time detection technique that does not use a separate probe that binds intermediate to the two primers is the KASPar detection system/method, which is well known in the art. In KASPar, two allele specific primers are designed such that the 3' nucleotide of each primer hybridizes to the polymorphic base. For example, if the SNP is an A/C polymorphism, one of the primers would have an "A" in the 3' position, while the other primer would have a "C" in the 3' position. Each of these two allele specific primers also has a unique tail sequence on the 5' end of the primer. A common reverse primer is employed that amplifies in conjunction with either of the two allele specific primers. Two 5' fluor-labeled reporter oligos are also included in the reaction mix, one designed to interact with each of the unique tail sequences of the allele-specific primers. Lastly, one quencher oligo is included for each of the two reporter oligos, the quencher oligo being complementary to the reporter oligo and being able to quench the fluor signal when bound to the reporter oligo. During PCR, the allele-specific primers and reverse primers bind to complementary DNA, allowing amplification of the amplicon to take place. During a subsequent cycle, a complementary nucleic acid strand containing a sequence complementary to the unique tail sequence of the allele-specific primer is created. In a further cycle, the reporter oligo interacts with this complementary tail sequence, acting as a labeled primer. Thus, the product created from this cycle of PCR is a fluorescently-labeled nucleic acid strand. Because the label incorporated into this amplification product is specific to the allele specific primer that resulted in the amplification, detecting the specific fluor presenting a signal can be used to determine the SNP allele that was present in the sample.

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook et al. *Molecular Cloning—A Laboratory Manual* (3d ed.) Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel"); and, *PCR Protocols A Guide to Methods and Applications* (Innis et al., eds) Academic Press Inc. San Diego, Calif. (1990) ("Innis"). Additional details regarding detection of nucleic acids in plants can also be found, e.g., in *Plant Molecular Biology* (1993) Croy (ed.) BIOS Scientific Publishers, Inc.

Other techniques for detecting SNPs can also be employed, such as allele specific hybridization (ASH) or nucleic acid sequencing techniques. ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Isolated polynucleotide or fragments thereof are capable of specifically hybridizing to other nucleic acid molecules under appropriate conditions. In one example, the nucleic acid molecules contain any of SEQ ID NOs: 1-5, complements thereof and fragments thereof. In another aspect, the nucleic acid molecules of the present disclosure include nucleic acid molecules that hybridize, for example, under high or low stringency, substantially homologous sequences, or that have both to these molecules. Conventional stringency conditions are described by Sambrook et al. In: Molecular Cloning, A Laboratory Manual, 2nd Edition, Cold Spring Harbor Press, Cold Spring Harbor, N.Y. (1989)), and by Haymes et al. In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In some examples, a marker locus will specifically hybridize to one or more of the nucleic acid molecules set forth in SEQ ID NOs: 1-5 or complements thereof or fragments of either under moderately stringent conditions, for example at about 2.0×SSC and about 65° C. In an aspect, a nucleic acid of the present disclosure will specifically hybridize to one or more SEQ ID NOs: 1-5 or complements or fragments of either under high stringency conditions.

In some examples, a marker associated with iron deficiency tolerance comprises any one of SEQ ID NOs: 1-5 or complements or fragments thereof. In other examples, a marker has between 80%, 85%, 90%, 91%, 92%, 93%, 94%, 95%, 96%, 97%, 98%, 99%, or 100% sequence identity to any one of SEQ ID NOs: 1-5 or complements or fragments thereof. Unless otherwise stated, percent sequence identity is determined using the GAP program default parameters for nucleic acid alignment (Accelrys, San Diego, Calif., USA).

Traits or markers are considered herein to be linked if they generally co-segregate. A $\frac{1}{100}$ probability of recombination per generation is defined as a map distance of 1.0 centiMorgan (1.0 cM). The genetic elements or genes located on a single chromosome segment are physically linked. In some aspects, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 9, 8, 7, 6, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 9%, 8%, 7%, 6%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

Markers are used to define a specific locus on the soybean genome. Each marker is therefore an indicator of a specific segment of DNA, having a unique nucleotide sequence. Map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in soybeans.

Favorable genotypes associated with at least one trait of interest may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis.

In some examples, markers within 1 cM, 5 cM, 10 cM, 15 cM, or 30 cM of SEQ ID NO: 1-5 are provided. Similarly, one or more markers mapped within 1, 5, 10, 20 and 30 cM or less from the markers provided can be used for the selection or introgression of the region associated with iron deficiency tolerance. In other examples, any marker that is linked with SEQ ID NOs: 1-5 and associated with iron deficiency is provided. In other examples, markers provided include a substantially a nucleic acid molecule within 5 kb, 10 kb, 20 kb, 30 kb, 100 kb, 500 kb, 1,000 kb, 10,000 kb, 25,000 kb, or 50,000 kb of a marker selected from the group consisting of SEQ ID NOs: 1-5.

Real-time amplification assays, including MB or TAQMAN® based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain examples, each allele-specific probe for a certain SNP locus is 13-18 nucleotides in length, dual-labeled with a florescence quencher at the 3' end and either the 6-FAM (6-carboxyfluorescein) or VIC (4,7,2'-trichloro-7'-phenyl-6-carboxyfluorescein) fluorophore at the 5' end.

To effectuate SNP allele detection, a real-time PCR reaction can be performed using primers that amplify the region including the SNP locus, the reaction being performed in the presence of all allele-specific probes for the given SNP locus. By then detecting signal for each detectable label employed and determining which detectable label(s) demonstrated an increased signal, a determination can be made of which allele-specific probe(s) bound to the amplicon and, thus, which SNP allele(s) the amplicon possessed. For instance, when 6-FAM- and VIC-labeled probes are employed, the distinct emission wavelengths of 6-FAM (518 nm) and VIC (554 nm) can be captured. A sample that is homozygous for one allele will have fluorescence from only the respective 6-FAM or VIC fluorophore, while a sample that is heterozygous at the analyzed locus will have both 6-FAM and VIC fluorescence.

Introgression of iron deficiency tolerance into less tolerant soybean germplasm is provided. Any method for introgressing a QTL or marker into soybean plants known to one of skill in the art can be used. Typically, a first soybean germplasm that contains tolerance to iron deficiency derived from a particular marker or haplotype and a second soybean germplasm that lacks such tolerance derived from the marker or haplotype are provided. The first soybean germplasm may be crossed with the second soybean germplasm to provide progeny soybean germplasm. These progeny germplasm are screened to determine the presence of iron deficiency tolerance derived from the marker or haplotype, and progeny that tests positive for the presence of tolerance derived from the marker or haplotype are selected as being soybean germplasm into which the marker or haplotype has been introgressed. Methods for performing such screening are well known in the art and any suitable method can be used.

One application of MAS is to use the tolerance markers or haplotypes to increase the efficiency of an introgression or backcrossing effort aimed at introducing a tolerance trait into a desired (typically high yielding) background. In marker assisted backcrossing of specific markers from a donor source, e.g., to an elite genetic background, one selects among backcross progeny for the donor trait and then uses repeated backcrossing to the elite line to reconstitute as much of the elite background's genome as possible.

Thus, the markers and methods can be utilized to guide marker assisted selection or breeding of soybean varieties with the desired complement (set) of allelic forms of chromosome segments associated with superior agronomic performance (tolerance, along with any other available markers for yield, disease tolerance, etc.). Any of the disclosed marker alleles or haplotypes can be introduced into a soybean line via introgression, by traditional breeding (or introduced via transformation, or both) to yield a soybean plant with superior agronomic performance. The number of alleles associated with tolerance that can be introduced or be present in a soybean plant ranges from 1 to the number of alleles disclosed herein, each integer of which is incorporated herein as if explicitly recited.

This also provides a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant that comprises at least one of the markers or haplotypes associated with tolerance, such that the progeny are capable of inheriting the marker or haplotype.

Often, a method is applied to at least one related soybean plant such as from progenitor or descendant lines in the subject soybean plants pedigree such that inheritance of the desired tolerance can be traced. The number of generations separating the soybean plants being subject to the methods will generally be from 1 to 20, commonly 1 to 5, and typically 1, 2, or 3 generations of separation, and quite often a direct descendant or parent of the soybean plant will be subject to the method (i.e., 1 generation of separation).

Genetic diversity is important for long-term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provides an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers, haplotypes, primers, and probes can be used for MAS involving crosses of elite lines to exotic soybean lines (elite X exotic) by subjecting the segregating progeny to MAS to maintain major yield alleles, along with the tolerance marker alleles herein.

As an alternative to standard breeding methods of introducing traits of interest into soybean (e.g., introgression), transgenic approaches can also be used to create transgenic plants with the desired traits. In these methods, exogenous nucleic acids that encode a desired QTL, marker, or haplotype are introduced into target plants or germplasm. For example, a nucleic acid that codes for an iron deficiency tolerance trait is cloned, e.g., via positional cloning, and introduced into a target plant or germplasm.

Experienced plant breeders can recognize iron deficiency tolerant soybean plants in the field, and can select the tolerant individuals or populations for breeding purposes or for propagation. In this context, the plant breeder recognizes "tolerant" and "non-tolerant" or "susceptible" soybean plants. However, plant tolerance is a phenotypic spectrum consisting of extremes in tolerance and susceptibility, as well as a continuum of intermediate tolerance phenotypes. Evaluation of these intermediate phenotypes using reproducible assays are of value to scientists who seek to identify genetic loci that impart tolerance, to conduct marker assisted selection for tolerant populations, and to use introgression techniques to breed a tolerance trait into an elite soybean line, for example.

To that end, screening and selection of tolerant soybean plants may be performed, for example, by exposing plants to iron deficiency in fields or field areas which have produced iron deficiency chlorosis symptoms in soybean consistently in past years, and selecting those plants showing tolerance to iron deficiency. An exemplary iron deficiency chlorosis scoring system is shown in the Examples (Example 1), but any other scoring system known in the art may be used (see, e.g., Wang et al. (2008) Theor Appl Genet 116:777-787).

In some examples, a kit for detecting markers or haplotypes, and/or for correlating the markers or haplotypes with a desired phenotype (e.g., iron deficiency tolerance), are provided. Thus, a typical kit can include a set of marker probes and/or primers configured to detect at least one favorable allele of one or more marker locus associated with tolerance, improved tolerance, or susceptibility to iron deficiency. These probes or primers can be configured, for example, to detect the marker alleles noted in the tables and examples herein, e.g., using any available allele detection format, such as solid or liquid phase array based detection, microfluidic-based sample detection, etc. The kits can further include packaging materials for packaging the probes, primers, or instructions; controls, such as control amplification reactions that include probes, primers, and/or template nucleic acids for amplifications; molecular size markers; or the like.

System or kit instructions that describe how to use the system or kit and/or that correlate the presence or absence of the allele with the predicted tolerance or susceptibility phenotype are also provided. For example, the instructions can include at least one look-up table that includes a correlation between the presence or absence of the favorable allele(s) and the predicted tolerance or improved tolerance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector.

Isolated nucleic acids comprising a nucleic acid sequence coding for tolerance or susceptibility to iron deficiency, or capable of detecting such a phenotypic trait, or sequences complementary thereto, are also included. In certain examples, the isolated nucleic acids are capable of hybridizing under stringent conditions to nucleic acids of a soybean cultivar phenotyped for iron deficiency tolerance, to detect loci associated with iron deficiency tolerance, including one or more of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, or Gm05:9080525. In some examples the isolated nucleic acids are markers, for example a marker of S29731-001-Q001. In some examples the nucleic acid is one of more polynucleotides selected from the group consisting of SEQ ID NOs: 1-5. In some examples the nucleic acid is a polynucleotides of SEQ ID NOs: 1. Vectors comprising one or more of such nucleic acids, expression products of such vectors expressed in a host compatible therewith, antibodies to the expression product (both polyclonal and monoclonal), and antisense nucleic acids are also included. In some examples, one or more of these nucleic acids is provided in a kit.

As the parental line having iron deficiency tolerance, any line known to the art or disclosed herein may be used. Also included are soybean plants produced by any of the foregoing methods. Seed of a soybean germplasm produced by crossing a soybean variety having a marker or haplotype associated with iron deficiency tolerance with a soybean variety lacking such marker or haplotype, and progeny thereof, is also included.

The present disclosure is illustrated by the following examples. The foregoing and following description of the present disclosure and the various examples are not intended to be limiting of the disclosure but rather are illustrative thereof. Hence, it will be understood that the disclosure is not limited to the specific details of these examples.

Non-limiting aspects include:

1. A method of detecting a first soybean plant or germplasm with improved iron deficiency tolerance, the method comprising detecting at least one favorable allele of one or more marker locus within 80 kb of a polynucleotide selected from the group consisting of:
   a) one or more marker loci on linkage group A1 selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525;
   b) a marker on linkage group A1 of S29731-001-Q001;
   c) one or more markers within a genomic DNA region selected from the group consisting of SEQ ID NOs: 1-5; and,
   d) one or more markers within a chromosome interval on linkage group A1 Gm05:9002800-Gm05:9097400.

2. The method of claim 1, wherein said detecting comprises detection of a haplotype comprising two or more markers selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525.

3. The method of claim 1, wherein said detecting comprises detection of a haplotype comprising marker S29731-001-Q001 and a second marker selected from the group consisting of Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525.

4. The method of claim 1, wherein said at least one favorable allele of one or more marker loci is selected from the group consisting of S29731 allele G, Gm05:9031274 allele G, Gm05:9032977 allele A, Gm05:9009488 allele G, Gm05:8897027 allele C, Gm05:8826919 allele T, Gm05:8912496 allele G, Gm05:8915863 allele C, Gm05:9011110 allele T, Gm05:9081402 allele G, Gm05:8912289 allele G, Gm05:8994830 allele C, Gm05:8912456 allele T, Gm05:8826615 allele G, Gm05:8810680 allele C, Gm05:9098413 allele A, Gm05:

8915641 allele T, Gm05:8912447 allele A, Gm05:8915642 allele A, Gm05:8915936 allele A, Gm05:8994518 allele A, Gm05:8911000 allele G, Gm05:8827043 allele C, Gm05:8808821 allele T, Gm05:8928168 allele C, Gm05:8913147 allele T, Gm05:9022152 allele A, Gm05:8822453 allele A, Gm05:8825498 allele C, Gm05:8814460 allele G, Gm05:8827199 allele C, Gm05:8827200 allele A, Gm05:8912397 allele T, Gm05:8809849 allele T, Gm05:8819720 allele T, Gm05:8826854 allele A, Gm05:8912668 allele C, Gm05:8818385 allele A, Gm05:8826076 allele G, Gm05:8913545 allele T, and Gm05:9080525 allele G.

5. The method of claim 1, wherein the detecting comprises amplifying the marker locus or a portion of the marker locus and detecting the resulting amplified marker amplicon.

6. The method of claim 5, wherein the amplifying comprises:
   a) admixing an amplification primer or amplification primer pair with a nucleic acid isolated from the first soybean plant or germplasm, wherein the primer or primer pair is complementary or partially complementary to at least a portion of the marker locus and is capable of initiating DNA polymerization by a DNA polymerase using the soybean nucleic acid as a template; and
   b) extending the primer or primer pair in a DNA polymerization reaction comprising a DNA polymerase and a template nucleic acid to generate at least one amplicon.

7. The method of claim 6, wherein the admixing of step 1) further comprises admixing at least one nucleic acid probe.

8. The method of claim 6, wherein the detection comprises PCR analysis.

9. The method of claim 1, further comprising selecting the first soybean plant or germplasm, or selecting a progeny of the first soybean plant or germplasm.

10. The method of claim 9, further comprising crossing the selected first soybean plant or germplasm with a second soybean plant or germplasm.

11. The method of claim 10, wherein the second soybean plant or germplasm comprises an exotic soybean strain or an elite soybean strain.

12. A kit for selecting at least one soybean plant, the kit comprising:
   a) primers or probes for detecting one or more marker loci associated with one or more quantitative trait loci associated with improved iron deficiency tolerance, wherein the one or more marker loci are selected from the group consisting of:
      i) one or more loci on linkage group A1 selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525; and
      ii) one or more markers within a genomic DNA region SEQ ID NOs: 1; and,
   b) instructions for using the primers or probes for detecting the one or more marker loci and correlating the detected marker loci with predicted improved tolerance or increased susceptibility to iron deficiency.

13. The kit of claim 12, wherein the primers or probes comprise one or more of SEQ ID NOs: 1-5.

14. An isolated polynucleotide capable of detecting a marker locus selected from the group consisting of S29731, Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525.

15. The isolated polynucleotide of claim 14, wherein the polynucleotide comprises a nucleotide sequence selected from the group consisting of SEQ ID NOs: 1-5.

16. An isolated polynucleotide capable of detecting a nucleotide polymorphism on soybean chromosome 5 wherein the polymorphism is at a genomic location selected from the group consisting of Gm05:9031274, Gm05:9032977, Gm05:9009488, Gm05:8897027, Gm05:8826919, Gm05:8912496, Gm05:8915863, Gm05:9011110, Gm05:9081402, Gm05:8912289, Gm05:8994830, Gm05:8912456, Gm05:8826615, Gm05:8810680, Gm05:9098413, Gm05:8915641, Gm05:8912447, Gm05:8915642, Gm05:8915936, Gm05:8994518, Gm05:8911000, Gm05:8827043, Gm05:8808821, Gm05:8928168, Gm05:8913147, Gm05:9022152, Gm05:8822453, Gm05:8825498, Gm05:8814460, Gm05:8827199, Gm05:8827200, Gm05:8912397, Gm05:8809849, Gm05:8819720, Gm05:8826854, Gm05:8912668, Gm05:8818385, Gm05:8826076, Gm05:8913545, and Gm05:9080525.

17. A method of soybean plant breeding comprising:
   a) crossing at least two different soybean parent plants, wherein the parent soybean plants differ in iron deficiency tolerance;
   b) obtaining a population of progeny soybean seed from said cross;
   c) genotyping the progeny soybean seed with at least one genetic marker; and,
   d) selecting a subpopulation comprising at least one soybean seed possessing a genotype for improved iron deficiency tolerance,
   wherein the mean iron deficiency tolerance of the selected subpopulation is improved as compared to the mean iron deficiency tolerance of the non-selected progeny subpopulation.

18. A method of soybean plant breeding comprising:
   a) crossing two different soybean parent plants, wherein the parent soybean plants differ in iron deficiency tolerance, and the parent soybean plant with higher iron deficiency tolerance has an earlier maturity adapted for a northern growing region;

b) obtaining progeny soybean seed from said cross;
c) genotyping the progeny seed of said cross with a genetic marker; and,
d) selecting progeny soybean seed possessing a genotype for improved iron deficiency tolerance.

19. The method of claim 18, wherein the parent plants differ in maturity by at least 10 days.

20. The method of claim 19, wherein the selected progeny soybean seed are adapted for a northern growing region.

EXAMPLES

Example 1

Soybean varieties were visually scored for symptoms of iron deficiency chlorosis at about the V3 stage (three nodes starting with the first unifoliate leaves), typically late June to mid-July in North America. The visual evaluation criteria and scoring scale are shown in Table 2.

Table 2

| Score | Symptoms |
|---|---|
| 9 | All plants are normal green color |
| 8 | A few plants are showing very light chlorosis on 1 or 2 leaves |
| 7 | <50% of the plants show mild chlorosis (light green leaves) |
| 6 | >50% of the plants show mild chlorosis, but no necrosis seen on leaves |
| 5 | Most plants are light green to yellow, no necrosis seen on leaves. Most plants are stunted ~50-75% of normal height |
| 4 | Most plants are yellow, necrosis seen on edges of less than half the leaves. Most plants are ~50% of normal height |
| 3 | Most plants are yellow, necrosis seen on most leaves. Most plants are ~20-40% of normal height |
| 2 | Most leaves are almost dead, most stems are still green. Plants are severely stunted ~10-20% of normal height |
| 1 | Most plants are completely dead. Live plants are ~10% of normal height, and have very little living tissue |

Example 2

Marker regression association analysis was used for fine-mapping of a locus conditioning tolerance to iron deficiency chlorosis in soybean. This analysis identified a region between Gm05:8808821-Gm05:9098412 (LG A1). Polymorphisms identified in this region were highly associated with the observed phenotypic variation across a panel of elite inbred soybean cultivars. Phenotypic data for iron chlorosis were collected during field studies as described in Example 1.

DNA was prepared using standard Illumina TruSeq Chemistry and lines were sequenced to ~0.5-40× genome coverage on an Illumina HiSeq2000. SNPs were called using proprietary software. The publicly available software R (available online at r-project.org) was used to conduct a regression association analysis on a set of 6944 SNPs identified in the region from Gm05:7500089-9854325 bp (physical positions are based on the Glyma1 Williams82 soybean reference assembly from JGI described in Schmutz et al. (2010) Nature 463:178-183). The association group comprised 637 proprietary soybean lines with known phenotypic scores.

The R-squared values generated in the regression analysis were plotted against the physical position of 6944 SNPs and reveals a peak of SNP-to-trait association between Gm05: 8808821-Gm05:9098413 suggesting a locus associated with iron chlorosis tolerance. The forty best associated SNPs on Gm05 (LG A1) explaining greater than 20% of the phenotypic variation are summarized in Table 3. Analysis statistics included the p-value of the F-test for regression (pv_Ftest) and R-squared (R2). A marker locus assay, S29731-001-Q001, was designed to detect the polymorphism at Gm05: 9031274.

TABLE 3

| | Allele (Genotype) | | | |
|---|---|---|---|---|
| Physical | Tolerant | Susceptible | pv_Ftest | R2 Value |
| 9031274 | GG | AA | 6.18E-50 | 0.300532 |
| 9032977 | AA | GG | 3.01E-49 | 0.297033 |
| 9009488 | GG | AA | 1.49E-40 | 0.251205 |
| 8897027 | CC | TT | 3.86E-38 | 0.237965 |
| 8826919 | TT | AA | 7.46E-38 | 0.236376 |
| 8912496 | GG | TT | 1.48E-37 | 0.234723 |
| 8915863 | CC | TT | 2.29E-37 | 0.233674 |
| 9011110 | TT | CC | 2.31E-37 | 0.233645 |
| 9081402 | GG | CC | 2.41E-37 | 0.233546 |
| 8912289 | GG | TT | 2.47E-36 | 0.227902 |
| 8994830 | CC | TT | 7.08E-36 | 0.225331 |
| 8912456 | TT | AA | 2.01E-35 | 0.222775 |
| 8826615 | GG | AA | 2.84E-35 | 0.221928 |
| 8810680 | CC | GG | 8.38E-35 | 0.219266 |
| 9098413 | AA | GG | 8.49E-35 | 0.219236 |
| 8915641 | TT | AA | 9.68E-35 | 0.218913 |
| 8912447 | AA | GG | 9.87E-35 | 0.218863 |
| 8915642 | AA | CC | 2.61E-34 | 0.216463 |
| 8915936 | AA | GG | 2.61E-34 | 0.216463 |
| 8994518 | AA | GG | 2.67E-34 | 0.216406 |
| 8911000 | GG | AA | 2.69E-34 | 0.216394 |
| 8827043 | CC | GG | 9.22E-34 | 0.213338 |
| 8808821 | TT | GG | 2.01E-33 | 0.211401 |
| 8928168 | CC | TT | 3.12E-33 | 0.210305 |
| 8913147 | TT | AA | 3.92E-33 | 0.209736 |
| 9022152 | AA | GG | 4.77E-33 | 0.209251 |
| 8822453 | AA | GG | 6.73E-33 | 0.20839 |
| 8825498 | CC | TT | 7.39E-33 | 0.208156 |
| 8814460 | GG | AA | 1.37E-32 | 0.206619 |
| 8827199 | CC | TT | 1.76E-32 | 0.20598 |
| 8827200 | AA | GG | 1.76E-32 | 0.20698 |
| 8912397 | TT | CC | 1.96E-32 | 0.205716 |
| 8809849 | TT | GG | 2.53E-32 | 0.205072 |
| 8819720 | TT | GG | 3.36E-32 | 0.204363 |
| 8826854 | AA | GG | 4.46E-32 | 0.203656 |
| 8912668 | CC | TT | 4.85E-32 | 0.203444 |
| 8818385 | AA | TT | 5.17E-32 | 0.203283 |
| 8826076 | GG | AA | 5.98E-32 | 0.202917 |
| 8913545 | TT | CC | 6.09E-32 | 0.202872 |
| 9080525 | GG | AA | 7.06E-32 | 0.202498 |

This marker, S29731-001-Q001 designed to detect the polymorphism at Gm05:9031274, was tested against an F3:4 population segregating for this locus. Three reps of 140 F3:4 individuals from the population were phenotyped and the lines genotyped. From this, phenotypic and genotypic data from 138 lines was available for analysis which confirmed the ability of the marker to distinguish between susceptible and resistant lines (ANOVA (Prob>F=0.0001). Additionally, the average effect of the marker (res-sus) was ¾ of a score in this population, which was determined to be significant using the paired Student's t-test. The average effect data is summarized in Table 4.

TABLE 4

| Class | Number | Mean | SE | Lower 95% | Upper 95% | Letter |
|---|---|---|---|---|---|---|
| Res | 55 | 4.59 | 0.08 | 4.42 | 4.75 | A |
| Het | 43 | 4.10 | 0.09 | 3.91 | 4.29 | B |
| Sus | 40 | 3.85 | 0.10 | 3.66 | 4.04 | B |

Example 3

From the analyses of marker loci associated with iron deficiency tolerance in soybean populations and varieties several markers were developed, tested, and confirmed, as summarized in the preceding tables. Any methodology can be deployed to use this information, including but not limited to any one or more of sequencing or marker methods.

In one example, sample tissue, including tissue from soybean leaves or seeds can be screened with the markers using a TAQMAN® PCR assay system (Life Technologies, Grand Island, N.Y., USA).

TAQMAN® Assay Conditions
Reaction Mixture (Total Volume=5 µl):

| | |
|---|---|
| Genomic DNA (dried) | 16 ng |
| DDH20 | 2.42 µl |
| Klearkall Mastermix | 2.5 µl |
| Forward primer (100 µM) | 0.0375 µl |
| Reverse primer (100 µM) | 0.0375 µl |
| Probe 1 (100 µM) | 0.005 µl |
| Probe 2 (100 µM) | 0.005 µl |

Reaction Conditions:

| | | |
|---|---|---|
| 94° C. | 10 min | 1 cycle |

40 cycles of the following:

| | |
|---|---|
| 94° C. | 30 sec |
| 60° C. | 60 sec |

Klearkall Mastermix is available from KBioscience Ltd. (Hoddesdon, UK).

The SNP markers identified in these studies could be useful, for example, for detecting and/or selecting soybean plants with improved tolerance to iron deficiency. The physical position of each SNP is provided in Table 3 based upon the JGI Glyma1 assembly (Schmutz et al. (2010) Nature 463:178-183). Any marker capable of detecting a polymorphism at one of these physical positions, or a marker associated, linked, or closely linked thereto, could also be useful, for example, for detecting and/or selecting soybean plants with improved iron deficiency tolerance. In some examples, the SNP allele present in the tolerant parental line could be used as a favorable allele to detect or select plants with improved tolerance. In other examples, the SNP allele present in the susceptible parent line could be used as an unfavorable allele to detect or select plants without improved tolerance.

These SNP markers could also be used to determine a favorable or unfavorable haplotype. In certain examples, a favorable haplotype would include any combinations of Gm05:9031274 allele G, and another favorable allele selected from the group consisting of Gm05:9032977 allele A, Gm05:9009488 allele G, Gm05:8897027 allele C, Gm05:8826919 allele T, Gm05:8912496 allele G, Gm05:8915863 allele C, Gm05:9011110 allele T, Gm05:9081402 allele G, Gm05:8912289 allele G, Gm05:8994830 allele C, Gm05:8912456 allele T, Gm05:8826615 allele G, Gm05:8810680 allele C, Gm05:9098413 allele A, Gm05:8915641 allele T, Gm05:8912447 allele A, Gm05:8915642 allele A, Gm05:8915936 allele A, Gm05:8994518 allele A, Gm05:8911000 allele G, Gm05:8827043 allele C, Gm05:8808821 allele T, Gm05:8928168 allele C, Gm05:8913147 allele T, Gm05:9022152 allele A, Gm05:8822453 allele A, Gm05:8825498 allele C, Gm05:8814460 allele G, Gm05:8827199 allele C, Gm05:8827200 allele A, Gm05:8912397 allele T, Gm05:8809849 allele T, Gm05:8819720 allele T, Gm05:8826854 allele A, Gm05:8912668 allele C, Gm05:8818385 allele A, Gm05:8826076 allele G, Gm05:8913545 allele T, and Gm05:9080525 allele G. In addition to the markers listed in Table 3, other closely linked markers could also be useful for detecting and/or selecting soybean plants with improved iron deficiency tolerance. Further, chromosome intervals containing the markers provided herein could also be used, the chromosome interval on linkage group A1 flanked by and including Gm05:9002800-Gm05:9097400, or an interval flanked by and including Gm05:7500089-Gm05:9854325, or an interval flanked by and including Gm05:8808821-Gm05:9098413. Other useful intervals include, for example the interval flanked by and including marker S29731-001 on LG-A1, or any interval provided in the Tables provided herein.

What is claimed is:

1. A method for producing a soybean plant or soybean germplasm having iron deficiency tolerance, the method comprising:
   a) crossing a first soybean plant or soybean germplasm with a second soybean plant or soybean germplasm to form a soybean plant or soybean germplasm population, wherein the first soybean plant or soybean germplasm is an elite line;
   b) isolating nucleic acids from the soybean plants or soybean germplasm of the population;
   c) detecting in the nucleic acids at least one maker loci associated with iron deficiency tolerance, wherein the at least one marker loci is selected from the group consisting of S29731 allele G, Gm05:9031274 allele G, Gm05:9032977 allele A, Gm05:9009488 allele G, Gm05:8897027 allele C, Gm05:8826919 allele T, Gm05:8912496 allele G, Gm05:8915863 allele C, Gm05:9011110 allele T, Gm05:9081402 allele G, Gm05:8912289 allele G, Gm05:8994830 allele C, Gm05:8912456 allele T, Gm05:8826615 allele G, Gm05:8810680 allele C, Gm05:9098413 allele A, Gm05:8915641 allele T, Gm05:8912447 allele A, Gm05:8915642 allele A, Gm05:8915936 allele A, Gm05:8994518 allele A, Gm05:8911000 allele G, Gm05:8827043 allele C, Gm05:8808821 allele T, Gm05:8928168 allele C, Gm05:8913147 allele T, Gm05:9022152 allele A, Gm05:8822453 allele A, Gm05:8825498 allele C, Gm05:8814460 allele G, Gm05:8827199 allele C, Gm05:8827200 allele A, Gm05:8912397 allele T, Gm05:8809849 allele T, Gm05:8819720 allele T, Gm05:8826854 allele A, Gm05:8912668 allele C, Gm05:8818385 allele A, Gm05:8826076 allele G, Gm05:8913545 allele T, and Gm05:9080525 allele G; and
   d) selecting, if present, one or more soybean plants or soybean germplasm of the population comprising the detected marker locus.

2. The method of claim 1, wherein the first soybean plant or first soybean germplasm and the second soybean plant or second soybean germplasm differ in iron deficiency tolerance.

3. The method of claim 1, wherein the detecting comprises detection of a haplotype comprising two or more markers.

4. The method of claim 1, wherein the detecting comprises amplifying the marker locus or a portion of the marker locus and detecting the resulting amplified marker amplicon.

5. The method of claim 4, wherein the amplifying comprises:
   a) admixing an amplification primer or amplification primer pair with a nucleic acid isolated from the first soybean plant or germplasm, wherein the primer or primer pair is complementary or partially complementary to at least a portion of the marker locus or flanking sequence and is capable of initiating DNA polymerization by a DNA polymerase using the soybean nucleic acid as a template; and b) extending the primer or primer pair in a DNA polymerization reaction comprising a DNA polymerase and a template nucleic acid to generate at least one amplicon.

6. The method of claim 5, wherein the admixing of step 1) further comprises admixing at least one nucleic acid probe.

7. The method of claim 5, wherein the detection comprises PCR analysis.

8. The method of claim 1, wherein the second soybean plant or germplasm comprises an exotic soybean strain or an elite soybean strain.

9. A method of introgression of iron deficiency tolerance into a soybean plant or soybean germplasm, the method comprising:

a) crossing at least one soybean plant or soybean germplasm tolerant to iron deficiency with at least one soybean plant or soybean germplasm susceptible to iron deficiency to form a soybean plant or soybean germplasm population, wherein the at least one soybean plant or soybean germplasm susceptible to iron deficiency comprises an elite line;

b) isolating nucleic acids from the soybean plants or soybean germplasm of the population;

c) detecting in the nucleic acids at least one maker loci associated with iron deficiency tolerance, wherein the at least one marker loci is selected from the group consisting of S29731 allele G, Gm05:9031274 allele G, Gm05:9032977 allele A, Gm05:9009488 allele G, Gm05:8897027 allele C, Gm05:8826919 allele T, Gm05:8912496 allele G, Gm05:8915863 allele C, Gm05:9011110 allele T, Gm05:9081402 allele G, Gm05:8912289 allele G, Gm05:8994830 allele C, Gm05:8912456 allele T, Gm05:8826615 allele G, Gm05:8810680 allele C, Gm05:9098413 allele A, Gm05:8915641 allele T, Gm05:8912447 allele A, Gm05:8915642 allele A, Gm05:8915936 allele A, Gm05:8994518 allele A, Gm05:8911000 allele G, Gm05:8827043 allele C, Gm05:8808821 allele T, Gm05:8928168 allele C, Gm05:8913147 allele T, Gm05:9022152 allele A, Gm05:8822453 allele A, Gm05:8825498 allele C, Gm05:8814460 allele G, Gm05:8827199 allele C, Gm05:8827200 allele A, Gm05:8912397 allele T, Gm05:8809849 allele T, Gm05:8819720 allele T, Gm05:8826854 allele A, Gm05:8912668 allele C, Gm05:8818385 allele A, Gm05:8826076 allele G, Gm05:8913545 allele T, and Gm05:9080525 allele G; and d) selecting, if present, one or more soybean plants of the population comprising the at least one detected marker loci.

10. The method of claim 9, wherein said detecting comprises detection of a haplotype comprising two or more markers.

11. The method of claim 9, wherein the detecting comprises amplifying the marker locus or a portion of the marker locus and detecting the resulting amplified marker amplicon.

12. The method of claim 11, wherein the amplifying comprises:

a) admixing an amplification primer or amplification primer pair with a nucleic acid isolated from the first soybean plant or germ plasm, wherein the primer or primer pair is complementary or partially complementary to at least a portion of the marker locus or flanking sequence and is capable of initiating DNA polymerization by a DNA polymerase using the soybean nucleic acid as a template; and b) extending the primer or primer pair in a DNA polymerization reaction comprising a DNA polymerase and a template nucleic acid to generate at least one amplicon.

13. The method of claim 12, wherein the admixing of step 1) further comprises admixing at least one nucleic acid probe.

14. The method of claim 12, wherein the detection comprises PCR analysis.

15. The method of claim 9, wherein the at least one soybean plant or soybean germ plasm tolerant to iron deficiency comprises an exotic soybean strain or an elite soybean strain.

* * * * *